United States Patent [19]

Neumann et al.

[11] Patent Number: 4,603,205
[45] Date of Patent: Jul. 29, 1986

[54] FURAN-3-CARBOXYLIC ACID DERIVATIVES

[75] Inventors: Peter Neumann, Wiesloch; Reinhard Helwig, Ludwigshafen; Stefan Weiss, Neckargemuend; Hubert Trauth, Dudenhofen, all of Fed. Rep. of Germany

[73] Assignee: BASF Aktiengesellschaft, Rheinland-Pfalz, Fed. Rep. of Germany

[21] Appl. No.: 681,195

[22] Filed: Dec. 13, 1984

[30] Foreign Application Priority Data

Dec. 15, 1983 [DE] Fed. Rep. of Germany ....... 3345376

[51] Int. Cl.⁴ ................ C07D 407/04; C07D 407/14
[52] U.S. Cl. ..................... 546/16; 546/187; 546/214
[58] Field of Search ................... 546/187, 214, 16

[56] References Cited

U.S. PATENT DOCUMENTS 4,021,432  5/1977  Holt et al. ........................ 546/187
4,075,165  2/1978  Soma et al. ........................ 546/16

FOREIGN PATENT DOCUMENTS

WO81/02021  7/1981  PCT Int'l Appl.
1318559  5/1973  United Kingdom.
1401924  8/1975  United Kingdom.

OTHER PUBLICATIONS

Waters et al, Chemical Abstracts, vol. 87 (1977) 161420y.
Chemical Abstracts Registry Handbook, 1977 Supplement, 64219 71-2.

Primary Examiner—Richard L. Raymond
Attorney, Agent, or Firm—Oblon, Fisher, Spivak, McClelland & Maier

[57] ABSTRACT

Novel furancarboxylic acid derivatives of the general formula

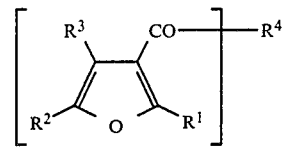

where $R^1$, $R^2$ and $R^3$ independently of one another are each hydrogen, $C_1$-$C_8$-alkyl, cyclohexyl or phenyl, but not more than two of these radicals are simultaneously hydrogen, and $R^4$ is a radical of the formula $-NR^5R^6$,

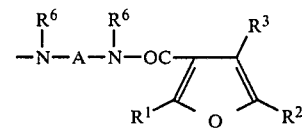

or $OR^6$, where A is a bridge member, $R^5$ is hydrogen, $C_2$-$C_6$-alkenyl, $C_5$-$C_7$-cycloalkyl or $C_1$-$C_{12}$-alkyl which may or may not be interrupted by 1, 2 or 3 oxygen atoms, and $R^6$ is a radical of the formula

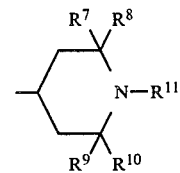

where $R^7$, $R^8$, $R^9$ and $R^{10}$ are each $C_1$-$C_4$-alkyl, or $R^7$ and $R^8$ or $R^9$ and $R^{10}$ together form a tetramethylene or pentamethylene bridge, and $R^{11}$ is hydrogen, $C_1$-$C_8$-alkyl, $C_3$-$C_8$-alkenyl, $C_2$-$C_4$-hydroxyalkyl or aralkyl, and their salts are useful as light stabilizers for organic polymers, in particular olefin polymers.

4 Claims, No Drawings

FURAN-3-CARBOXYLIC ACID DERIVATIVES

It is known that 2,2,6,6-tetraalkylpiperidine derivatives are excellent light stabilizers for organic polymers. Among these compounds, furancarboxylic acid derivatives have also been disclosed.

German Laid-Open Application DOS No. 2,258,752 describes tetraalkylpiperidinyl esters of furan-2-carboxylic acid and of furan-2,5-dicarboxylic acid. The publication WO 81 02 021 mentions the tri-(2,2,6,6-tetramethylpiperidin-4-yl) ester of a furantricarboxylic acid which is not defined exactly. Finally, German Laid-Open Application DOS No. 2,623,422 describes tetraalkylpiperidinyl furan-2-carboxylates.

German Pat. No. 2,040,975 claims tetraalkylpiperidinylamides of furan-2-carboxylic acid and of furan-2,3,4-tricarboxylic acid, while German Pat. No. 2,349,962 describes pentaalkylpiperidinylamides of furan-2-carboxylic acid.

The 2,2,6,6-tetraalkylpiperidin-4-yl furancarboxylates described to date have in common at least a carboxyl group in the 2-position of the heterocyclic ring. Surprisingly, we have found that the stabilizing action of the novel 2,2,6,6-tetraalkylpiperidin-4-yl derivatives of alkyl-substituted furan-3-carboxylic acids is substantially superior to that of the corresponding furan-2-carboxylic acid derivatives.

The present invention relates to furancarboxylic acid derivatives of the general formula

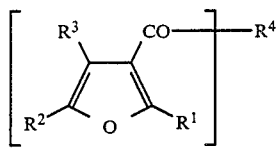

where $R^1$, $R^2$ and $R^3$ independently of one another are each hydrogen, $C_1$–$C_8$-alkyl, cyclohexyl or phenyl, but not more than two of these radicals are simultaneously hydrogen, and $R^4$ is a radical of the formula

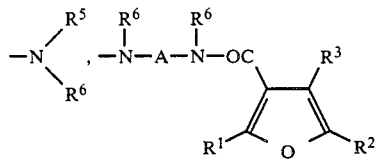

or $OR^6$, where A is a bridge member, $R^5$ is hydrogen, $C_2$–$C_6$-alkenyl, $C_5$–$C_7$-cycloalkyl or $C_1$–$C_{12}$-alkyl which may or may not be interrupted by 1, 2 or 3 oxygen atoms, and $R^6$ is a radical of the formula

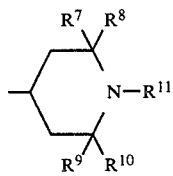

where $R^7$, $R^8$, $R^9$ and $R^{10}$ are each $C_1$–$C_4$-alkyl, or $R^7$ and $R^8$ or $R^9$ and $R^{10}$ together form a tetramethylene or pentamethylene bridge, and $R^{11}$ is hydrogen, $C_1$–$C_8$-alkyl, $C_3$–$C_8$-alkenyl, $C_2$–$C_4$-hydroxyalkyl or aralkyl, and their salts.

Alkyl radicals $R^1$, $R^2$, $R^3$, $R^5$, $R^7$, $R^8$, $R^9$, $R^{10}$ and $R^{11}$ are defined generally as straight-chain or branched groups $C_nH_{2n+1}$, the straight-chain radicals being preferred. Specific examples are

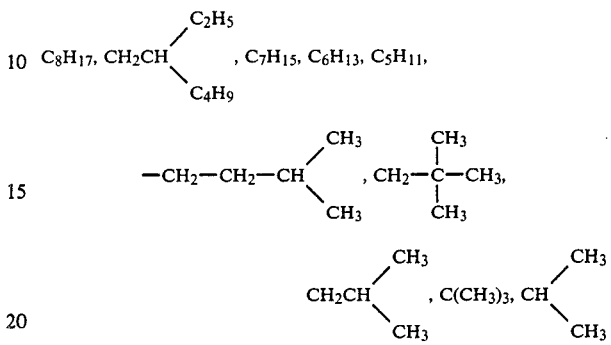

and preferably $CH_3$, $C_2H_5$, $C_3H_7$ and $C_4H_9$.

Examples of alkyl groups $R^5$ containing ether oxygen are $(CH_2)_3OCH_3$, $(CH_2)_3OC_2H_5$, $(CH_2)_3OC_3H_7$, $(CH_2)_3OC_4H_9$, $(CH_2)_2O(CH_2)_2OCH_3$, $(CH_2)_2O(CH_2)_2OC_2H_5$, $(CH_2)_2O(CH_2)_2OC_3H_7$, $(CH_2)_3O(CH_2)_2OC_4H_9$, $(C_2H_4O)_3CH_3$, $(C_2H_4O_3)C_2H_5$, $(C_2H_4O)_3C_4H_9$,

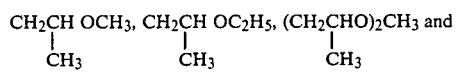

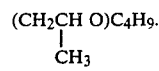

Examples of alkenyl groups are vinyl, allyl, methallyl and but-2-enyl.

Examples of cycloalkyl radicals $R^5$ are cyclopentyl, cyclohexyl and cycloheptyl.

Examples of alkenyl, hydroxyalkyl and aralkyl radicals $R^{11}$ are $CH_2CH=CH_2$,

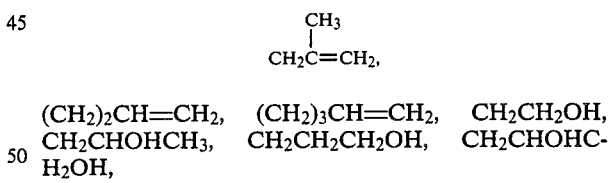

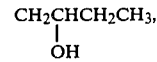

$CH_2C_6H_5$, $C_2H_4C_6H_5$, $CH_2C_6H_4CH_3$ and $CH_2C_6H_4Cl$.

Bridge members A are, in particular, $C_2$–$C_{12}$-alkylene group which may contain one or more ether oxygen atoms, aralkylene, cycloalkylene and $C_6$–$C_{16}$-alkylene chain interrupted by cycloalkyl, as exemplary radicals of the formulae

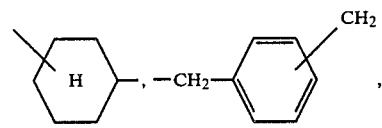

-continued

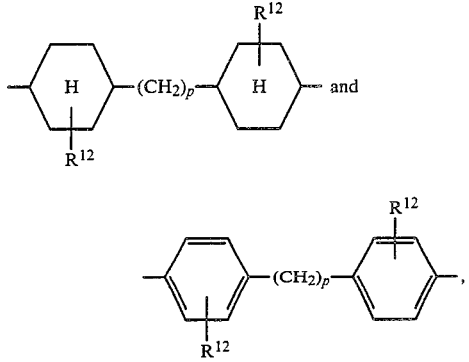

where $R^{12}$ is hydrogen or methyl and p is 0, 1 or 2.

Specific examples of alkylene radicals are $C_2H_4$, $(CH_2)_3$, $(CH_2)_4$, $(CH_2)_6$, $(CH_2)_2O(CH_2)_2$, $(CH_2)_3O(CH_2)_3$ and $(CH_2)_3O(CH_2)_2O(CH_2)_3$.

In preferred compounds of the formula I, $R^1$, $R^2$ and $R^3$ are each hydrogen or methyl, and $R^7$, $R^8$, $R^9$ and $R^{10}$ are each methyl.

The derivatives based on 2,4— or 2,5-dimethylfuran-3-carboxylic acid or on 2,4,5-trimethylfuran-3-carboxylic acid are particularly preferred.

Other particularly preferred compounds are those in which $R^1$, $R^2$, $R^7$, $R^8$, $R^9$ and $R^{10}$ are each $CH_3$ and $R^3$ is H.

The compounds according to the invention can be prepared by well-known chemical processes. For example, the piperidinyl furancarboxylates can be prepared either from the corresponding acyl halides and the 4-hydroxy-2,2,6,6-tetraalkylpiperidines in the presence of an acid acceptor, such as an organic amine or an alkali metal hydroxide, or from the corresponding methyl or ethyl esters by transesterification with a 4-hydroxy-2,2,6,6-tetraalkylpiperidine in the presence of a catalytic compound, such as an alkali metal alcoholate or titanium tetrabutylate. The amides are advantageously prepared via the acyl halides.

The preparation of the furan-3-carboxylic acid derivatives required as starting compounds is known from the literature. For example, methyl 2,5-dimethylfuran-3-carboxylate can be prepared by the methods described in German Laid-Open Applications DOS No. 2,207,098 and DOS No. 2,826,013.

Ethyl 2-methyl-5-ethylfuran-3-carboxylate and corresponding esters with higher alkyl groups in the 5—position of the furan ring are described in J. Org. Chem. 43 (1978), 4596.

Ethyl 2-methyl-5-phenylfuran-3-carboxylate can be prepared by the method described in Bull. Soc. Chim. France 1970, [6], 2272.

Methyl 2,4-dimethylfuran-3-carboxylate and methyl 2,4,5-trimethylfuran-3-carboxylate can be prepared by for example, the method described in Anales real soc.' espan. fis. y quim. (Madrid) 50 B (1954), 407–412 [C.A. 49 (1955), 13 207 c].

Methyl 2-methyl-4-ethylfuran-3-carboxylate can be prepared similarly to methyl 2,4-dimethylfuran-3-carboxylate, by using 1-hydroxybutan-2-one instead of hydroxyacetone.

The synthesis of methyl 2-methylfuran-3-carboxylate is described in, for example, German Laid-Open Application DOS No. 2,800,505 and J. Chem. Soc., Perkin Trans. I, 1981, pages 1982–1989.

Methods for the preparation of other alkyl-substituted furan-3-carboxylates are described in the literature.

The preparation of the acyl chlorides can be carried out by a conventional method, for example by hydrolyzing the methyl or ethyl esters of the corresponding acids to the free acids and then reacting these with thionyl chloride or another suitable compound to give the acyl chlorides.

The compounds according to the invention can be in the form of the free base or of a salt. Suitable anions are derived from, for example, inorganic acids and, in particular, organic carboxylic acids.

Examples of inorganic anions are chloride, bromide, sulfate, methosulfate, phosphate and thiocyanate.

Examples of carboxylic acid anions are formate, acetate, propionate, hexanoate, cyclohexanoate, lactate, stearate, dodecylbenzoate, benzoate, acrylate, methacrylate, citrate, malonate and succinate, and anions of polycarboxylic acids containing not more than 3000 COOH groups.

The Examples which follow describe the preparation.

The compounds according to the invention are useful for stabilizing organic material, especially plastics, to degradation by light and heat. They are added to the plastics being stabilized in a concentration of from 0.01 to 5, preferably from 0.02 to 1, % by weight, before, during or after polymer formation.

To mix the novel compounds with the plastics being stabilized, any conventional apparatus or method for mixing stabilizers or other additives into polymers can be used.

The plastics stabilized by means of one of the novel compounds can, if required, contain further additives, for example antioxidants, light stabilizers, metal deactivators, antistatic agents, flame retardants, pigments or fillers.

Examples of antioxidants and light stabilizers which can be added to the plastics in addition to the novel compounds are compounds based on sterically hindered phenols, and costabilizers containing sulfur or phosphorus.

Examples of phenolic antioxidants of this type are 2,6-di-tert.-butyl-4-methylphenol, n-octadecyl-$\beta$-(3,5-di-tert.-butyl-4-hydroxyphenyl)-propionate, 1,1,3-tris-(2-methyl-4-hydroxy-5-tert.-butylphenyl)-butane, 1,3,5-trimethyl-2,4,6-tris-(3,5-di-tert.-butyl-4-hydroxybenzyl)-benzene, 1,3,5-tris-(3,5-di-tert.-butyl-4-hydroxybenzyl)isocyanurate, 1,3,5-tris-[$\beta$-(3,5-di-tert.-butyl-4-hydroxyphenyl)-propionyloxyethyl]ioscyanurate, 1,3,5-tris-(2,6-dimethyl-3-hydroxy-4-tert.-butylbenzyl)isocyanurate, pentaerythritol tetrakis-[$\beta$-(3,5-di-tert.-butyl-4-hydroxyphenyl)-propionate], etc.

Examples of phosphorus-containing antioxidants are tris-(nonylphenyl)-phosphite, distearyl pentaerythritol diphosphite, tris-(2,4-di-tert.-butylphenyl)phosphite, tris-(2-tert.-butyl-4-methylphenyl)phosphite, bis-(2,4-di-tert.-butylphenyl)pentaerythritol diphosphite, tetrakis-(2,4-di-tert.-butylphenyl) 4,4'-biphenylene diphosphite, etc.

Examples of sulfur-containing antioxidants are dilauryl thiodipropionate, dimyristyl thiodipropionate, distearyl thiodipropionate, pentaerythritol tetrakis-($\beta$-laurylthiopropionate), pentaerythritol tetrakis-($\beta$-hexylthiopropionate), etc.

Examples of other antioxidants and light stabilizers which can be used together with the compounds according to the invention are 2-(2'-hydroxyphenyl)-benzotriazoles, 2-hydroxybenzophenones, aryl esters of hydroxybenzoic acids, α-cyanocinnamic acid derivatives, nickel compounds and oxalic acid dianilides.

Examples of organic polymers which can be stabilized by means of the compounds according to the invention are polymers of mono- and diolefins, such as low-density or high-density polyethylene, linear low-density polyethylene, polypropylene, polyisobutylene, polybut-1-ene, polymethylpent-1-ene, polyisoprene or polybutadiene, and copolymers of mono- or diolefins, or blends of the stated polymers; copolymers of mono- or diolefins with other vinyl monomers, eg. ethylene/alkyl acrylate, ethylene/alkyl methacrylate, ethylene/vinyl acetate or ethylene/acrylic acid copolymers; polystyrene; copolymers of styrene or α-methylstyrene with dienes or acrylyl derivatives, eg. styrene/butadiene, styrene/acrylonitrile, styrene/ethyl methacrylate, styrene/butadiene/ethyl acrylate or styrene/acrylonitrile/methyl acrylate; ABS, MBS or similar polymers; halogen-containing polymers, eg. polyvinyl chloride, polyvinyl fluoride or polyvinylidene fluoride, and copolymers of these; polymers derived from α,β-unsaturated acids and their derivatives, eg. polyacrylates, polymethacrylates, polyacrylamides and polyacrylonitriles; polymers derived from unsaturated alcohols and amines or their acyl derivatives or acetals, eg. polyvinyl alcohol or polyvinyl acetate; and polyurethanes, nylons, polyureas, polyesters, polycarbonates, polysulfones and polyether-sulfones.

Other organic polymers which can be stabilized using the compounds according to the invention are industrial finishes. Particularly noteworthy among these are baking finishes, among which in turn automotive finishes, preferably two-coat finishes.

In this case, too, the antioxidants and light stabilizers stated above can additionally be used.

Solid compounds according to the invention can be added to the finish in solid or dissolved form, while liquid compounds according to the invention can be added as such to the finish. Their good solubility in the surface coating systems is particularly advantageous.

The compounds according to the invention are preferably used in polyolefins, preferably ethylene polymers and propylene polymers.

EXAMPLE 1

2,2,6,6-tetramethylpiperidin-4-yl
2,5-dimethylfuran-3-carboxylate 154 g (1 mole) of methyl 2,5-dimethylfuran-3-carboxylate and 157 g (1 mole) of 4-hydroxy-2,2,6,6-tetramethylpiperidine were heated together with 10 g of tetrabutyl orthotitanate for 10 hours at about 190° C., the methanol formed being distilled off. When the reaction is complete, the mixture is cooled and the reaction mass is dissolved in ethyl acetate. The solution is extracted by shaking, first with 10% strength sodium carbonate solution and then with water, after which it is dried and evaporated down, and the residue is distilled under reduced pressure. The desired product distils at 142° C./2 mm as a virtually colorless oil which soon solidifies to a solid of melting point 59°-61° C.

EXAMPLE 2

1,2,2,6,6-pentamethylpiperidin-4-yl
2,5-dimethylfuran-3-carboxylate

If, in Example 1, 4-hydroxy-1,2,2,6,6-pentamethylpiperidine is used instead of 4-hydroxy-2,2,6,6-tetramethylpiperidine, the product obtained is a virtually colorless oil of boiling point 120°-122° C./0.15 mm.

EXAMPLE 3

2,2,6,6-tetramethylpiperidin-4-yl
2,4-dimethylfuran-3-carboxylate

If, in Example 1, methyl 2,4-dimethylfuran-3-carboxylate is used instead of methyl 2,5-dimethylfuran-3-carboxylate, the product obtained is a virtually colorless oil of boiling point 136°-138° C./1 mm.

EXAMPLE 4

2,2,6,6-tetramethylpiperidin-4-yl
2,4,5-trimethylfuran-3-carboxylate

If, in Example 1, methyl 2,4,5-trimethylfuran-3-carboxylate is used instead of methyl 2,5-dimethylfuran-3-carboxylate, the product obtained is a virtually colorless oil of boiling point 137°-139° C./0.5 mm; this soon solidifies to a solid of melting point 54°-58° C.

EXAMPLE 5

1,2,2,6,6-pentamethylpiperidin-4-yl
2,4,5-trimethylfuran-3-carboxylate

If methyl 2,4,5-trimethylfuran-3-carboxylate and 4-hydroxy-1,2,2,6,6-pentamethylpiperidine are reacted by the method given in Example 1, the product obtained is a virtually colorless oil of boiling point 138°-140° C./0.4 mm; this solidifies to a solid of melting point 55°-56° C.

EXAMPLE 6

2,5-dimethylfuran-3-carboxylic acid
2,2,6,6-tetramethylpiperidin-4-ylamide 156 g (1 mole) of 4-amino-2,2,6,6-tetramethylpiperidine and 79 g (0.5 mole) of 2,5-dimethylfuran-3-carbonyl chloride in 1 l of toluene are refluxed for 24 hours, after which the precipitate is filtered off, the toluene solution is extracted by shaking with NaHCO$_3$ solution and water, and is dried and evaporated down, and the residue is recrystallized from cyclohexane to give a product of melting point 116°-118° C.

EXAMPLE 7

2,2,6,6-tetramethyl-N-(2-hydroxyethyl)-piperidin-4-yl
2,5-dimethylfuran-3-carboxylate 50 g of the product described in Example 1 are reacted with ethylene oxide in 50% strength aqueous ethanol in an autoclave at from 110° to 120° C. and under an initial pressure of 6 bar, and the reaction is terminated when the pressure has fallen to 1 bar.

The product obtained is purified by stirring thoroughly with water. It is obtained as a virtually white solid of melting point 83°-85° C.

EXAMPLE 8

2,5-dimethylfuran-3-carboxylic acid
N-butyl-N-(2,2,6,6-tetramethylpiperidin-4-yl)-amide 158.5 g (1 mole) of 2,5-dimethylfuran-3-carbonyl chloride and 212 g (2 moles) of 4-N-butylamino-2,2,6,6-tetramethylpiperidine in 1.5 l of toluene are refluxed with 55 g of anhydrous sodium carbonate for 24 hours. The mixture is left to cool, and the precipitate is filtered off under suction and stirred with 1 l of water, and the mixture is extracted twice with 0.5 l of ethyl acetate.

The combined ethyl acetate phases are dried, and evaporated down under reduced pressure from a water pump, the crystalline residue is suspended in a little petroleum ether, and the product is filtered off under suction and dried. It has a melting point of 78°–79° C. and is pure according to gas chromatography.

EXAMPLE 9

2,5-dimethylfuran-3-carboxylic acid N-butyl-N-(1,2,2,6,6-pentamethylpiperidin-4-yl)-amide 100.2 g (0.3 mole) of 2,5-dimethylfuran-3-carboxylic acid N-butyl-N-(2,2,6,6-tetramethylpiperidin-4-yl)-amide (Preparation Example 8) are refluxed with 100 g of 37% strength aqueous formaldehyde solution and 30 g of formic acid for 7 hours.

The mixture is cooled, 1 l of water is added and the mixture is rendered alkaline with 5% strength aqueous potassium hydroxide solution and then extracted twice with 0.5 l of ethyl acetate. The combined ethyl acetate phases are dried over $MgSO_4$ and evaporated down under reduced pressure from a water pump. The product remains behind as a pale yellow oil.

EXAMPLE 10

Bis-(N-1,6-Hexamethylene-N-2,2,6,6-tetramethylpiperidin-4-yl)-2,5-dimethylfuran-3-carboxamide 158.5 g (1 mole) of 2,5-dimethylfuran-3-carbonyl chloride and 197 g (0.5 mole) of bis-4-(1,6-hexamethylene)-amino-2,2,6,6-tetramethylpiperidine in 1.5 l of toluene are refluxed together with 55 g of anhydrous sodium carbonate for 24 hours, after which the mixture is left to cool, the precipitate is filtered off under suction, dried at 80° C. under reduced pressure and then stirred into 2 l of water, and the suspension is rendered alkaline with dilute sodium hydroxide solution. The precipitate is filtered off under suction, washed neutral with a little water and dried at 80° C. under reduced pressure. After recrystallization from cyclohexane, the product has a melting point of 162°–164° C.

EXAMPLE 11

Salt of bis-(N-1,6-hexamethylene-N-2,2,6,6-tetramethylpiperidin-4-yl)-2,5-dimethylfuran-3-carboxamide with polyacrylic acid containing about 70 units.

64 g (0.1 mole) of the carboxamide from Preparation Example 10 and 7.2 g of powdered polyacrylic acid which has been carefully dehydrated and has a molecular weight of about 5000, in methanol, are stirred with gentle heating until a clear solution has formed. The solution is evaporated to dryness under reduced pressure from a water pump, and the residue is powdered. It has a melting point of 156°–158° C.

Other compounds according to the invention are listed in Tables 1 to 5. The symbols relate to Formula I.

TABLE 1

$R^1 = R^2 = CH_3; R^3 = H$

| Example | $R^4$ | Mp. or Bp. |
|---|---|---|
| 12 | as in Example 1, salt of 2,4-dimethylglutaric acid | 156–158° C. |
| 13 | as in Example 1, salt of adipic acid | 176–178° C. |
| 14 | as in Example 1, salt of polyacrylic acid (about 28–42 units) | 115–120° C. |
| 15 | as in Example 1, salt of polyacrylic acid (about 70 units) | 148–150° C. |
| 16 | as in Example 1, salt of polyacrylic acid (about 2100–2800 units) | about 300° C. |
| 17 | as in Example 6, salt of 2,4-dimethylglutaric acid | 180–182° C. |
| 18 | as in Example 6, salt of polyacrylic acid (about 28–42 units) | 122–126° C. |
| 19 | as in Example 6, salt of polyacrylic acid (about 70 units) | 156–158° C. |
| 20 | —NH—[2,2,6,6-tetramethyl-N-CH₃-piperidin-4-yl] | 126–128° C. |
| 21 | as in Example 8, salt of 2,4-dimethylglutaric acid | 143–145° C. |
| 22 | as in Example 8, salt of adipic acid | |
| 23 | as in Example 8, salt of polyacrylic acid (about 28–42 units) | 78–82° C. |
| 24 | as in Example 8, salt of polyacrylic acid (about 70 units) | 80–82° C. |
| 28 | —N(2,2,6,6-tetramethylpiperidin-4-yl)—CH₂—CH(CH₃)—N(2,2,6,6-tetramethylpiperidin-4-yl)— | |
| 29 | —N(2,2,6,6-tetramethylpiperidin-4-yl)—C₆H₁₀—CH₂—C₆H₁₀—N(2,2,6,6-tetramethylpiperidin-4-yl)— | 72–6° C. |
| 30 | —N(2,2,6,6-tetramethylpiperidin-4-yl)—(3-CH₃-C₆H₉)—CH₂—(3-CH₃-C₆H₉)—N(2,2,6,6-tetramethylpiperidin-4-yl)— | |
| 31 | —N(1,2,2,6,6-pentamethylpiperidin-4-yl)—(CH₂)₂—N(1,2,2,6,6-pentamethylpiperidin-4-yl)— | |
| 32 | —N(1,2,2,6,6-pentamethylpiperidin-4-yl)—(CH₂)₆—N(1,2,2,6,6-pentamethylpiperidin-4-yl)— | |

TABLE 1-continued $R^1 = R^2 = CH_3; R^3 = H$

| Example | R⁴ | Mp. or Bp. |
|---|---|---|
| 33 | [structure: two 2,2,6,6-tetramethyl-1-methyl-piperidin-4-yl groups linked via -N-cyclohexyl-CH₂-cyclohexyl-N-] | |
| 34 | [structure: two 2,2,6,6-tetramethylpiperidin-4-yl (NH) groups linked via -N-CH₂-C₆H₄-CH₂-N-] | |
| 35 | [structure: two 2,2,6,6-tetramethylpiperidin-4-yl (NH) groups linked via -N-(CH₂)₃O(CH₂)₂O(CH₂)₃-N-] | |

TABLE 2

$R^1 = R^3 = CH_3; R^2 = H$

| Example | R⁴ | Mp. or Bp. |
|---|---|---|
| 36 | as in Example 3, salt of adipic acid | 182–4° C. |
| 37 | as in Example 3, salt of polyacrylic acid (about 70 units) | 132–5° C. |
| 38 | [structure: -O-piperidine with N—CH₃] | 120° C./0.3 mm |
| 39 | [structure: -NH-piperidine-NH] | 170–3° C. |
| 40 | as in Example 39, salt of adipic acid | 178–80° C. |
| 41 | [structure: -NH-piperidine with N—CH₃] | |
| 42 | [structure: -N(C₄H₉)-piperidine-NH] | 100–2° C. |
| 43 | as in Example 42, salt of adipic acid | |

TABLE 2-continued $R^1 = R^3 = CH_3; R^2 = H$

| Example | R⁴ | Mp. or Bp. |
|---|---|---|
| 44 | [structure: -N(C₄H₉)-piperidine with N—CH₃] | |
| 45 | [structure: two piperidine (NH) groups linked via -N-(CH₂)₂-N-] | |
| 46 | [structure: two piperidine (NH) groups linked via -N-(CH₂)₆-N-] | 172–4° C. |
| 47 | [structure: two piperidine (NH) groups linked via -N-CH₂-CH(CH₃)-N-] | |
| 48 | [structure: two piperidine (NH) groups linked via -N-cyclohexyl-CH₂-cyclohexyl-N-] | 128–30° C. |
| 49 | [structure: -N((CH₂)₃OCH₃)-piperidine-NH] | 78–79° C. |

TABLE 3

$R^1 = R^2 = R^3 = CH_3$

| Example | R⁴ | Mp. or Bp. |
|---|---|---|
| 50 | as in Example 4, salt of adipic acid | 170–2° C. |
| 51 | as in Example 4, salt of polyacrylic acid (about 70 units) | 142–6° C. |
| 52 | [structure: -O-piperidine with N—CH₃] | 55–6° C. 138–40° C./0.4 mm |

TABLE 3-continued $R^1 = R^2 = R^3 = CH_3$

| Example | R⁴ | Mp. or Bp. |
|---|---|---|
| 53 | —NH—[piperidinyl]—NH—[piperidinyl] | 150–5° C. |
| 54 | —N(C₄H₉)—[piperidinyl]—NH—[piperidinyl] | |
| 55 | —N(—[NH-piperidinyl])—(CH₂)₆—N—(—[NH-piperidinyl]) | |
| 56 | —N(—[NCH₃-piperidinyl])—(CH₂)₆—N—(—[NCH₃-piperidinyl]) | |

TABLE 4

$R^1 = CH_3; R^2 = R^3 = H$

| Example | R⁴ | Mp. or Bp. |
|---|---|---|
| 57 | —O—[piperidinyl]—NH | viscous |
| 58 | as in Example 57, salt of polyacrylic acid (about 70 units) | 135–40° C. |
| 59 | —NH—[piperidinyl]—NH | |
| 60 | —N(C₄H₉)—[piperidinyl]—NH | |
| 61 | —N(—[NH-piperidinyl])—(CH₂)₆—N—(—[NH-piperidinyl]) | |

TABLE 5

Derivatives of various furancarboxylic acids

| Example | R¹ | R² | R³ | R⁴ | Mp. or bp. |
|---|---|---|---|---|---|
| 62 | CH₃ | H | C₂H₅ | —O—[piperidinyl]—NH | 50–2° C. |
| 63 | CH₃ | H | C₂H₅ | —O—[piperidinyl]—N—CH₃ | 180–6° C./ 0.5 mm |
| 64 | CH₃ | H | C₂H₅ | —N(C₄H₉)—[piperidinyl]—NH | |
| 65 | CH₃ | C₂H₅ | H | —O—[piperidinyl]—NH | |
| 66 | CH₃ | C₂H₅ | H | —N(C₄H₉)—[piperidinyl]—NH | |
| 67 | CH₃ | C₆H₅ | H | —O—[piperidinyl]—NH | 103–5° C. |

USE EXAMPLES (1) Stabilization of polyethylene with the compound from Example 1

(a) 0.25 part of the compound from Example 1 are incorporated in 100 parts of low-density polyethylene (1840 D from BASF) by extruding twice at 180° C., and the product is pressed to give 200 um thick sheets. After storage in the dark at 25° C. for 14 days, the surface of the sheets does not exhibit any coating.

(b) The sheets produced as described in (a) are tested in respect of their stability to weathering in a QUV accelerated weathering test apparatus. Ageing is determined by measuring the CO number after certain time intervals. Embrittlement is considered to have begun when the CO number reaches 10. The test results are summarized in Table 1. For comparison, 2,2,6,6-tetramethylpiperidin-4-yl furan-2-carboxylate is tested under the same conditions.

Test specimens are prepared using the compounds from Examples 2, 3 and 8, the method used being similar to that described in Example (1a). These specimens are tested by a method similar to that described in Example (1b), and the results are summarized in Table 1.

TABLE 1

| Compound | Exposure time in hours | | | | | | | | |
|---|---|---|---|---|---|---|---|---|---|
| | 500 | 1000 | 1500 | 2000 | 2500 | 3000 | 3500 | 4000 | 4500 |
| Example 1 | 0.33 | 0.5 | 0.77 | 1.55 | 7.4 | 10 | | | |
| Example 2 | 0.30 | 0.51 | 0.68 | 1.1 | 3.5 | 10 | | | |
| Example 3 | | 0.18 | 0.24 | 0.48 | 0.90 | 1.83 | 2.56 | 3.39 | 7.08 |
| Example 8 | | 0.24 | 0.41 | 1.03 | 2.01 | 3.75 | 7.74 | | |
| Example 21 | | 0.07 | 0.13 | 0.17 | 0.25 | | | | |
| Example 67 | | 0.22 | 0.32 | 0.49 | 0.94 | | | | |
| 2,2,6,6-tetramethylpiperidin-4-yl furan-2-carboxylate | 0.5 | 1.55 | 6.07 | | | | | | |
| without a stabilizer | 5 | | | | | | | | |

(2) Stabilization of polypropylene (a) 0.25 part of the compound from the appropriate Example are incorporated in 100 parts of polypropylene (1320 H from BASF) by extruding twice at 220° C., and the product is pressed to give 200 μm thick sheets. After storage in the dark at 25° C. for 14 days, the surface of the sheets does not exhibit any coating.

(b) The sheets produced as described in (a) are tested in respect to their stability to weathering in a QUV accelerated weathering test apparatus. Ageing is determined by measuring the CO number after certain time intervals, and the beginning of embrittlement is examined mechanically. The test results are summarized in Table 2.

TABLE 2

| Compound | Time until embrittlement occurs in h |
|---|---|
| Example 6 | 1730 |
| Example 8 | 1920 |
| Example 10 | 1740 |
| Example 11 | 1770 |
| Example 21 | 1700 |
| Example 25 | 1720 |
| Example 26 | 2000 |
| Example 27 | 1770 |
| Example 29 | 1620 |
| Example 39 | 1920 |
| Example 53 | 1740 |
| 2,2,6,6-tetramethyl-piperidin-4-yl furan-2-carboxylate | 950 |

We claim:

1. A furancarboxylic acid derivative of the formula:

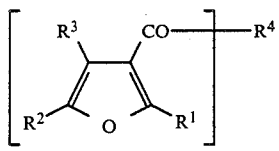

(I)

where $R^1$, $R^2$ and $R^3$ independently of one another are each hydrogen, $C_1$–$C_8$-alkyl, cyclohexyl or phenyl, but not more than two of these radicals are simultaneously hydrogen, and $R^4$ is a radical of the formula

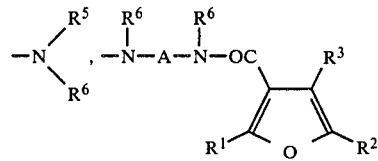

or $OR^6$, where A is a bridge member selected from the group consisting of straight-chain or branched $C_2$–$C_{12}$-alkylene group which may contain one or more ether oxygen atoms, aralkylene, cycloalkylene and $C_6$–$C_{16}$-alkylene chain interrupted by cycloalkyl, $R^5$ is hydrogen, $C_2$–$C_6$-alkenyl, $C_5$–$C_7$-cycloalkyl or $C_1$–$C_{12}$-alkyl which may or may not be interrupted by 1, 2 or 3 oxygen atoms, and $R^6$ is a radical of the formula

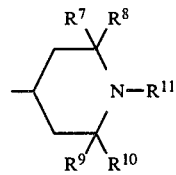

where $R^7$, $R^8$, $R^9$ and $R^{10}$ are each $C_1$–$C_4$-alkyl, or $R^7$ and $R^8$ or $R^9$ and $R^{10}$ together form a tetramethylene or pentamethylene bridge, and $R^{11}$ is hydrogen, $C_1$–$C_8$-alkyl, $C_3$–$C_8$-alkenyl, $C_2$–$C_4$-hydroxyalkyl or aralkyl, and its salts.

2. A compound as claimed in claim 1, wherein $R^7$, $R^8$, $R^9$ and $R^{10}$ are each methyl.

3. A compound as claimed in claim 1, wherein $R^{11}$ is hydrogen or methyl.

4. A piperidinyl ester or amide as claimed in claim 1, which is based on 2,4— or 2,5-dimethylfuran-3-carboxylic acid or on 2,4,5-trimethylfuran-3-carboxylic acid.

* * * * *